United States Patent
Bohana-Kashtan

(10) Patent No.: US 11,090,337 B2
(45) Date of Patent: *Aug. 17, 2021

(54) PREPARATION OF PHOTORECEPTORS FOR THE TREATMENT OF RETINAL DISEASES

(71) Applicant: CELL CURE NEUROSCIENCES LTD, Jerusalem (IL)

(72) Inventor: Osnat Bohana-Kashtan, Tel-Mond (IL)

(73) Assignee: CELL CURE NEUROSCIENCES LTD, Jerusalem (IL)

( * ) Notice: Subject to any disclaimer, the term of this patent is extended or adjusted under 35 U.S.C. 154(b) by 85 days.

This patent is subject to a terminal disclaimer.

(21) Appl. No.: 15/750,049

(22) PCT Filed: Aug. 4, 2016

(86) PCT No.: PCT/IL2016/050856
§ 371 (c)(1),
(2) Date: Feb. 2, 2018

(87) PCT Pub. No.: WO2017/021972
PCT Pub. Date: Feb. 9, 2017

(65) Prior Publication Data
US 2018/0228846 A1 Aug. 16, 2018

Related U.S. Application Data

(60) Provisional application No. 62/201,132, filed on Aug. 5, 2015, provisional application No. 62/253,739, filed on Nov. 11, 2015.

(51) Int. Cl.
*A61K 35/30* (2015.01)
*C12N 5/07* (2010.01)
*C12N 5/079* (2010.01)
*C12N 5/0793* (2010.01)
*A01N 1/02* (2006.01)

(52) U.S. Cl.
CPC .............. *A61K 35/30* (2013.01); *C12N 5/062* (2013.01); *C12N 5/0621* (2013.01); *A01N 1/0221* (2013.01); *C12N 2500/02* (2013.01); *C12N 2500/38* (2013.01); *C12N 2501/15* (2013.01); *C12N 2501/16* (2013.01); *C12N 2506/02* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 5,755,785 A | 5/1998 | Rowsey et al. |
| 5,843,780 A | 12/1998 | Thomson |
| 5,941,250 A | 8/1999 | Aramant et al. |
| 5,962,027 A | 10/1999 | Hughes |
| 6,045,791 A | 4/2000 | Liu |
| 6,090,622 A | 7/2000 | Gearhart et al. |
| 7,267,981 B2 | 9/2007 | Amit et al. |
| 8,956,886 B2 | 2/2015 | Idelson et al. |
| 2011/0027333 A1* | 2/2011 | Idelson ............... A61K 9/0051 424/423 |
| 2013/0196369 A1 | 8/2013 | Hikita et al. |
| 2015/0368713 A1* | 12/2015 | Bharti ............... G01N 33/5058 506/9 |

FOREIGN PATENT DOCUMENTS

| | | |
|---|---|---|
| CN | 101688178 A | 3/2010 |
| EP | 2128244 A1 | 12/2009 |
| GB | 2327675 A | 2/1999 |
| WO | 01/55114 A1 | 8/2001 |
| WO | 02/060875 A1 | 8/2002 |
| WO | 03/068233 A1 | 8/2003 |
| WO | 2005/014549 A1 | 2/2005 |

(Continued)

OTHER PUBLICATIONS

International Preliminary Report on Patentability received for PCT/IL2016/050856, dated Feb. 15, 2018, 8 pages.
International Search Report and Written Opinion received for PCT/IL2016/050856, dated Nov. 29, 2016, 10 pages.
Algvere et al. (Mar. 1997) "Transplantation of RPE in Age-related Macular Degeneration: Observations in Disciform Lesions and Dry RPE Atrophy", Graefe's Archive for Clinical and Experimental Ophthalmology, 235 (3):149-158.
Aoi et al. (Aug. 1, 2008) "Generation of Pluripotent Stem Cells From Adult Mouse Liver and Stomach Cells", Science, 321(5889):699-702.
Bigar et al. (Aug. 1992) "Corneal Transplantation", Current Opinion in Ophthalmology, 3(4):473-481.
Bongs() et al. (Aug. 1989) "Improved Quality of Human Embryos when Co-Cultured with Human Ampullary Cells", Human Reproduction, 4(6):706-713.

(Continued)

*Primary Examiner* — Michelle F. Paguio Frising

(57) ABSTRACT

A method of generating photoreceptors is disclosed. Cell populations comprising photoreceptors and uses thereof are also disclosed.

19 Claims, 7 Drawing Sheets

(56) References Cited

FOREIGN PATENT DOCUMENTS

| WO | 2006/040763 | A2 | 4/2006 | |
|---|---|---|---|---|
| WO | 2006/070370 | A2 | 7/2006 | |
| WO | 20081129554 | A1 | 10/2008 | |
| WO | WO-2013114360 | A1 * | 8/2013 | ........... C12N 5/0621 |
| WO | 2013/184809 | A1 | 12/2013 | |
| WO | 2016/108219 | A1 | 7/2016 | |
| WO | 2016/108239 | A1 | 7/2016 | |
| WO | 2016/108240 | A1 | 7/2016 | |

OTHER PUBLICATIONS

Burdon et al. (1995) "A Survey of Corneal Graft Practice in the United Kingdom", Eye, 9(Suppl.):6-12.

Chacko et al. (Feb. 24, 2000) "Survival and Differentiation of Cultured Retinal Progenitors Transplanted in the Subretinal Space of the Rat", Biochemical and Biophysical Research Communications, 268(3):842-846.

Chung et al. (Feb. 7, 2008) "Human Embryonic Stem Cell Lines Generated without Embryo Destruction", Cell Stem Cell, 2(2):113-117.

Doetschman et al. (May 1988) "Establishment of Hamster Blastocyst-Derived Embryonic Stem (ES) Cells", Developmental Biology, 127(1):224-227.

Gardner et al. (Jan. 1998) "Culture and Transfer of Human Blastocysts Increases Implantation Rates and Reduces the Need for Multiple Embryo Transfers", Fertility and Sterility, 69(1):84-88.

Giles et al. (Oct. 1993) "Pluripotency of Cultured Rabbit Inner Cell Mass Cells Detected by Isozyme Analysis and Eye Pigmentation of Fetuses Following Injection into Blastocysts or Morulae", Molecular Reproduction and Development, 36(2):130-138.

Graves et al. (Dec. 1993) "Derivation and Characterization of Putative Pluripotential Embryonic Stem Cells from Preimplantation Rabbit Embryos", Molecular Reproduction and Development, 36(4):424-433.

Iannaccone et al. (May 1994) "Pluripotent Embryonic Stem Cells from the Rat Are Capable of Producing Chimeras", Developmental Biology, 163(1):288-292.

Kalkan et al. (Dec. 2014) "Mapping the Route From Naive Pluripotency to Lineage Specification", Philosophical Transactions of the Royal Society B Biological Sciences, 20130540, 369(1657):10 pages.

Lamba et al. (Jan. 2010) "Generation, Purification and Transplantation of Photoreceptors Derived from Human Induced Pluripotent Stem Cells", Plos One, e8763, 5(1):9 pages.

Mitalipova et al. (2001) "Pluripotency of Bovine Embryonic Cell Line Derived from Precompacting Embryos", Cloning, 3(2):59-67.

Notarianni et al. (1991) "Derivation of Pluripotent, Embryonic Cell Lines from the Pig and Sheep", Journal of Reproduction and Fertility Supplement, 43:255-260.

Oplinger et al. (Apr. 1998) "A Comparison of Corneal Autografts With Homografts", Ophthalmic Surgery, Lasers and Imaging Retina, 29(4):305-308.

Park et al. (Feb. 2008) "Reprogramming of Human Somatic Cells to Pluripotency With Defined Factors", Nature, 451(7175):141-146.

Patel et al. (Apr. 2000) "Indications for and Outcomes of Repeat Penetrating Keratoplasty, 1989-1995", Ophthalmology, 107(4):719-724.

Peyman et al. (Feb. 1991) "A Technique for Retinal Pigment Epithelium Transplantation for Age-related Macular Degeneration Secondary to Extensive Subfoveal Scarring", Ophthalmic Surgery, Lasers and Imaging Retina, 22 (2):102-108(9 pages).

Reubinoff et al. (Apr. 2000) "Embryonic Stem Cell Lines from Human Blastocysts: Somatic Differentiation in Vitro", Nature Biotechnology, 18(4):399-404.

Richards et al. (Sep. 2002) "Human Feeders Support Prolonged Undifferentiated Growth of Human Inner Cell Masses and Embryonic Stem Cells", Nature Biotechnology, 20(9):933-936.

Shamblott et al. (Nov. 1998) "Derivation of Pluripotent Stem Cells from Cultured Human Primordial Germ Cells", Proceedings of the National Academy of Sciences, 95(23):13726-13731.

Sieving et al. (Mar. 7, 2006) "Ciliary Neurotrophic Factor (CNTF) for Human Retinal Degeneration: Phase I Trial of CNTF Delivered by Encapsulated Cell Intraocular Implants", Proceedings of the National Academy of Sciences, 103 (10):3896-3901.

Takahashi et al. (Nov. 30, 2007) "Induction of Pluripotent Stem Cells from Adult Human Fibroblasts by Defined Factors", Cell, 131(5):861-872.

Thomson et al. (Nov. 6, 1998) "Embryonic Stem Cell Lines Derived from Human Blastocysts", Science, 282 (5391):1145-1147.

Thomson et al. (Aug. 1995) "Isolation of a Primate Embryonic Stem Cell Line", Proceedings of the National Academy of Sciences, 92(17):7844-7848.

Thomson et al. (Aug. 1996) "Pluripotent Cell Lines Derived from Common Marmoset (*Callithrix jacchus*) Blastocysts", Biology of Reproduction, 55(2):254-259.

Thomson et al. (1998) "Primate Embryonic Stem Cells", Current Topics in Developmental Biology, 38:133-165.

Tsubota (Nov.-Dec. 1999) "Ocular Surface Management in Corneal Transplantation, a Review", Japanese Journal of Ophthalmology, 43(6):502-508.

Wheeler (1994) "Development and Validation of Swine Embryonic Stem Cells: A Review", Reproduction, Fertility and Development, 6(5):563-568.

Yamanaka (Jul. 2007) "Strategies and New Developments in the Generation of Patient-specific Pluripotent Stem Cells", Cell Stem Cell, 1(1):39-49.

Zhou et al. (Jun. 2011) "Differentiation of Induced Pluripotent Stem Cells of Swine into Rod Photoreceptors and their Integration into the Retina", Stem Cells, 29(6):972-980.

Buchholz et al. (Apr. 18, 2013) "Rapid and Efficient Directed Differentiation of Human Pluripotent Stem Cells Into Retinal Pigmented Epithelium", Stem Cells Translational Medicine, 2(5):384-393.

* cited by examiner

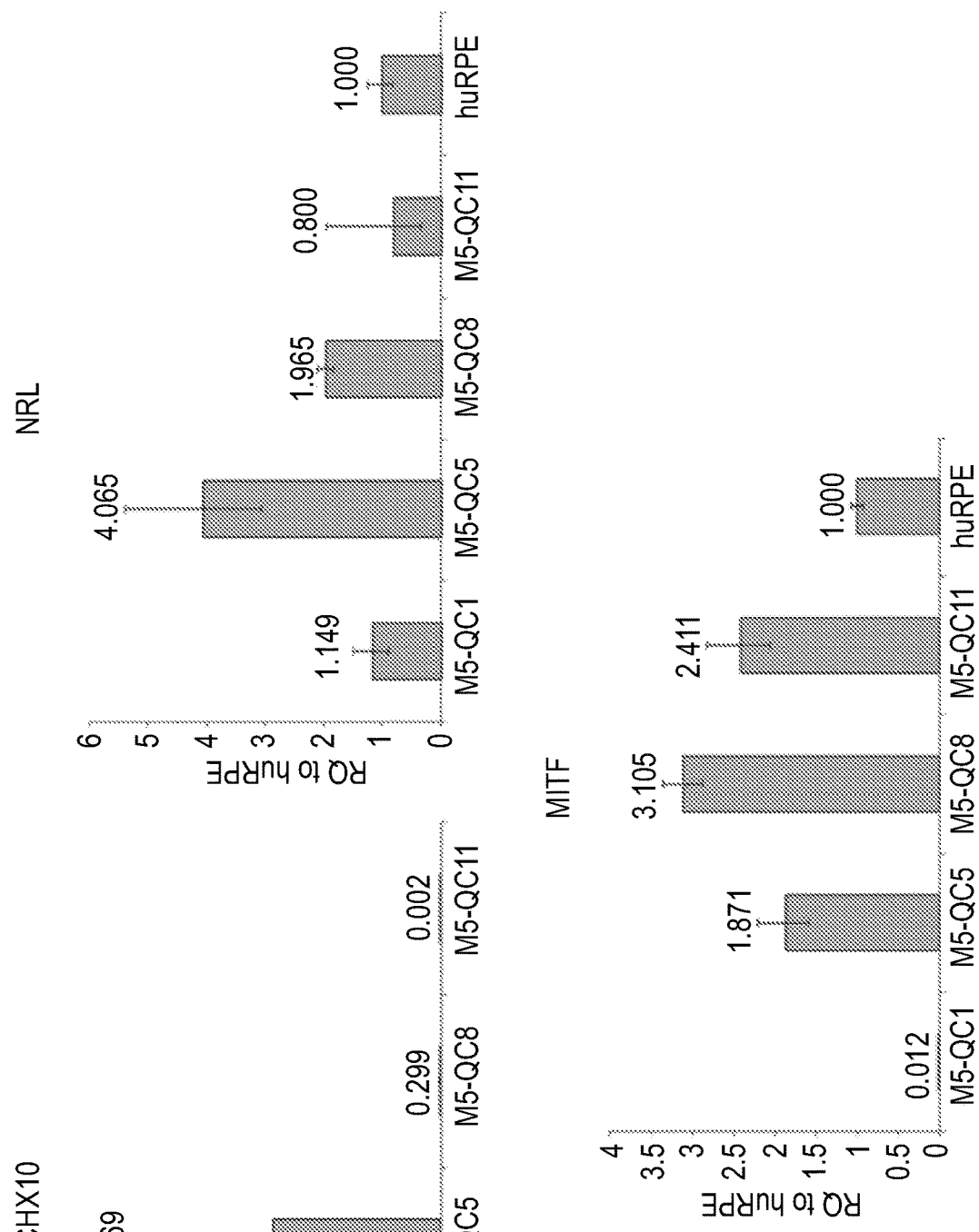

PREPARATION OF PHOTORECEPTORS FOR THE TREATMENT OF RETINAL DISEASES

CROSS-REFERENCE TO RELATED APPLICATIONS

This application is a National Phase Application of PCT/IL2016/050856, filed Aug. 4, 2016, which claims benefit under 35 USC § 119(e) to U.S. Provisional Application No. 62/201,132, filed Aug. 5, 2015 and U.S. Provisional Application No. 62/253,739, filed Nov. 11, 2015, which are incorporated herein by reference in their entirety.

FIELD AND BACKGROUND OF THE INVENTION

The present invention, in some embodiments thereof, relates to methods of preparing photoreceptors from pluripotent stem cells.

Various ocular diseases, including retinitis pigmentosa and age-related macular degeneration, are characterized by a loss of photoreceptor cells, leading to blindness. Once photoreceptors have degenerated, cell replacement or prosthetic devices are the only therapeutic options. Photoreceptor cell replacement has been shown feasible, even in mature mice, where photoreceptors transplanted to the subretinal space integrated into the retina and functioned (MacLaren et al., 2006). Several protocols (2D and 3D) have been developed for derivation of retinal progenitors and photoreceptors from human embryonic stem cells (Osakada et al., 2008; Meyer et al., 2009 and 2011; Nakano et al., 2012; Gonzalez-Cordero et al., 2013; Zhong et al., 2014).

Additional background art includes WO 2013/114360, WO 2008/129554 and WO 2013/184809.

SUMMARY OF THE INVENTION

According to an aspect of the present invention there is provided a method of treating a retinal disease in a subject in need thereof comprising:
(a) culturing a population of human pluripotent stem cells in a medium comprising a differentiating agent to obtain differentiating cells;
(b) culturing the differentiating cells in a culture system comprising a medium which comprises one or more members of the TGFβ superfamily, thereby generating a mixed population of cells comprising retinal pigment epithelial (RPE) cells and photoreceptors;
(c) enriching for the photoreceptors in the mixed population of cells so as to generate a photoreceptor-enriched population of cells; and
(d) administering a therapeutically effective amount of the photoreceptor-enriched population of cells to the subject, thereby treating the retinal disease.

According to an aspect of the present invention there is provided a method of generating photoreceptors comprising:
(a) culturing a population of human pluripotent stem cells in a medium comprising a differentiating agent to obtain differentiating cells;
(b) culturing the differentiating cells in a culture system comprising a medium which comprises one or more members of the TGFβ superfamily, thereby generating a mixed population of cells comprising retinal pigment epithelial (RPE) cells and photoreceptors;
(c) enriching for the photoreceptors in the mixed population of cells so as to generate a photoreceptor-enriched population of cells; and
(d) expanding the photoreceptor-enriched population of cells.

According to an aspect of the present invention there is provided a method of treating a retinal disease or disorder in a subject in need thereof comprising administering a therapeutically effective amount of the population of photoreceptors described herein to the subject thereby treating the retinal disease or disorder.

According to an aspect of the present invention there is provided a method of treating a retinal disease in a subject in need thereof comprising:
(a) culturing a population of human pluripotent stem cells in a medium comprising a differentiating agent to obtain differentiating cells;
(b) culturing the differentiating cells in a culture system comprising a medium which comprises one or more members of the TGFβ superfamily, thereby generating a mixed population of cells comprising retinal pigment epithelial (RPE) cells and photoreceptors, wherein at least 10% of the mixed population of cells are photoreceptors; and
(c) administering a therapeutically effective amount of the mixed population of cells to the subject, thereby treating the retinal disease.

According to an aspect of the present invention there is provided a population of photoreceptors generated as described herein.

According to embodiments of the present invention, step (c) is effected by mechanical isolation.

According to embodiments of the present invention, less than 80% of all the cells in the enriched population of cells are RPE cells.

According to embodiments of the present invention, the method further comprises expanding the human pluripotent stem cells prior to step (a).

According to embodiments of the present invention, the method further comprises expanding the population of photoreceptors following step (c) and prior to step (d).

According to embodiments of the present invention, the method further comprises cryopreserving the photoreceptors following step (c) and prior to step (d).

According to embodiments of the present invention, the method further comprises cryopreserving the photoreceptors following step (d).

According to embodiments of the present invention, the method further comprises cryopreserving the mixed population of cells following step (b) and prior to step (c).

According to embodiments of the present invention, the cryopreserving is effected in a medium selected from the group consisting of 90% Human Serum/10% DMSO, CryoStor 10%, CryoStor® 5%, CryoStor® 2%, Stem Cellbanker® and Prime XV® FreezIS.

According to embodiments of the present invention, the human pluripotent stem cells comprise human embryonic stem cells (ESCs) or induced pluripotent stem cells (iPSCs).

According to embodiments of the present invention, the differentiating agent comprises nicotinamide.

According to embodiments of the present invention, the medium of step (a) is devoid of activin A.

According to embodiments of the present invention, the member of the TGFβ superfamily is selected from the group consisting of TGFβ1, TGFβ3 and activin A.

According to embodiments of the present invention, the medium of step (b) comprises nicotinamide and activin A.

According to embodiments of the present invention, the method further comprises a step of culturing the photoreceptors in a medium comprising nicotinamide and devoid of activin A following step (b) and prior to step (c).

According to embodiments of the present invention, the step (a) is effected under non-adherent conditions.

According to embodiments of the present invention, the non-adherent conditions comprise a non-adherent culture plate.

According to embodiments of the present invention, the non-adherent conditions comprise a non-adherent substrate.

According to embodiments of the present invention, step (a) comprises:

i) culturing the cultured population of human pluripotent stem cells in a medium comprising nicotinamide, in the absence of activin A under non-adherent conditions to generate a cluster of cells comprising differentiating cells; and subsequently;

ii) culturing the differentiating cells of (i) in a medium comprising nicotinamide, in the absence of activin A under adherent conditions.

According to embodiments of the present invention, the method further comprises dissociating the cluster of cells prior to step (ii) to generate clumps of cells or a single cell suspension of cells.

According to embodiments of the present invention, the step (a) is effected for at least one day.

According to embodiments of the present invention, the step (b) is effected for at least one day.

According to embodiments of the present invention, at least a portion of the culturing is effected under conditions wherein the atmospheric oxygen level is less than about 10%.

According to embodiments of the present invention, the culturing is effected under conditions wherein the atmospheric oxygen level is greater than about 10%.

According to embodiments of the present invention, the human pluripotent stem cells are expanded on feeder cells.

According to embodiments of the present invention, the feeder cells comprise human cord fibroblasts.

According to embodiments of the present invention, the transplanting is effected at the subretinal space of the eye.

According to embodiments of the present invention, the cells are transplanted in a suspension, or as a monolayer of cells immobilized on a matrix or a substrate.

According to embodiments of the present invention, the retinal disease or disorder is selected from at least one of retinitis pigmentosa, lebers congenital amaurosis, hereditary or acquired macular degeneration, age related macular degeneration (AMD), Best disease, retinal detachment, gyrate atrophy, choroideremia, pattern dystrophy, RPE dystrophies, Stargardt disease, RPE and retinal damage due to damage caused by any one of photic, laser, inflammatory, infectious, radiation, neovascular or traumatic injury.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2E illustrates that MITF relative expression is increased during expansion of RPE, as expected. M4, Mock 4; QC, in process quality control; HAD102c: HAD-C 102 hESCs; huRPE: Human embryonic RPE (commercial, ScienCell); M4-QC1: Mock 4 HAD-C 102-hESCs following manual passaging; M4-QC2: HAD-C 102-hESCs following collagenase passaging; M4-QC4: Mock 4 cells after 2 weeks with nicotinamide activin A; M4-QC5: Mock 4 cells at the end of the differentiation phase with nicotinamide and activin A; M4-QC8: Mock 4 cells at passage P0 (1 expansion cycle); M4-QC11: Mock 4 cells at passage P2 post cryopreservation (Drug Product).

FIGS. 3A-D are graphs illustrating the upregulation of Chx10 (FIG. 3A), Nrl (FIG. 3B), MITF (FIG. 3C) and Rhodopsin (FIG. 3D) following differentiation of hESCs with Nicotinamide and activin A. M5, Mock 5; QC, in process quality control; HAD102c: HAD-C 102 hESCs; huRPE: Human embryonic RPE (commercial, ScienCell); M5-QC1: Mock 5 HAD-C 102-hESCs following mechanical expansion; M5-QC5: Mock 5 cells at the end of the differentiation phase with nicotinamide and activin A; M5-QC8: Mock 5 cells at passage P0 (1 expansion cycle); M5-QC11: Mock 5 cells at passage P2 post cryopreservation (Drug Product).

DESCRIPTION OF SPECIFIC EMBODIMENTS OF THE INVENTION

Figure 1A:
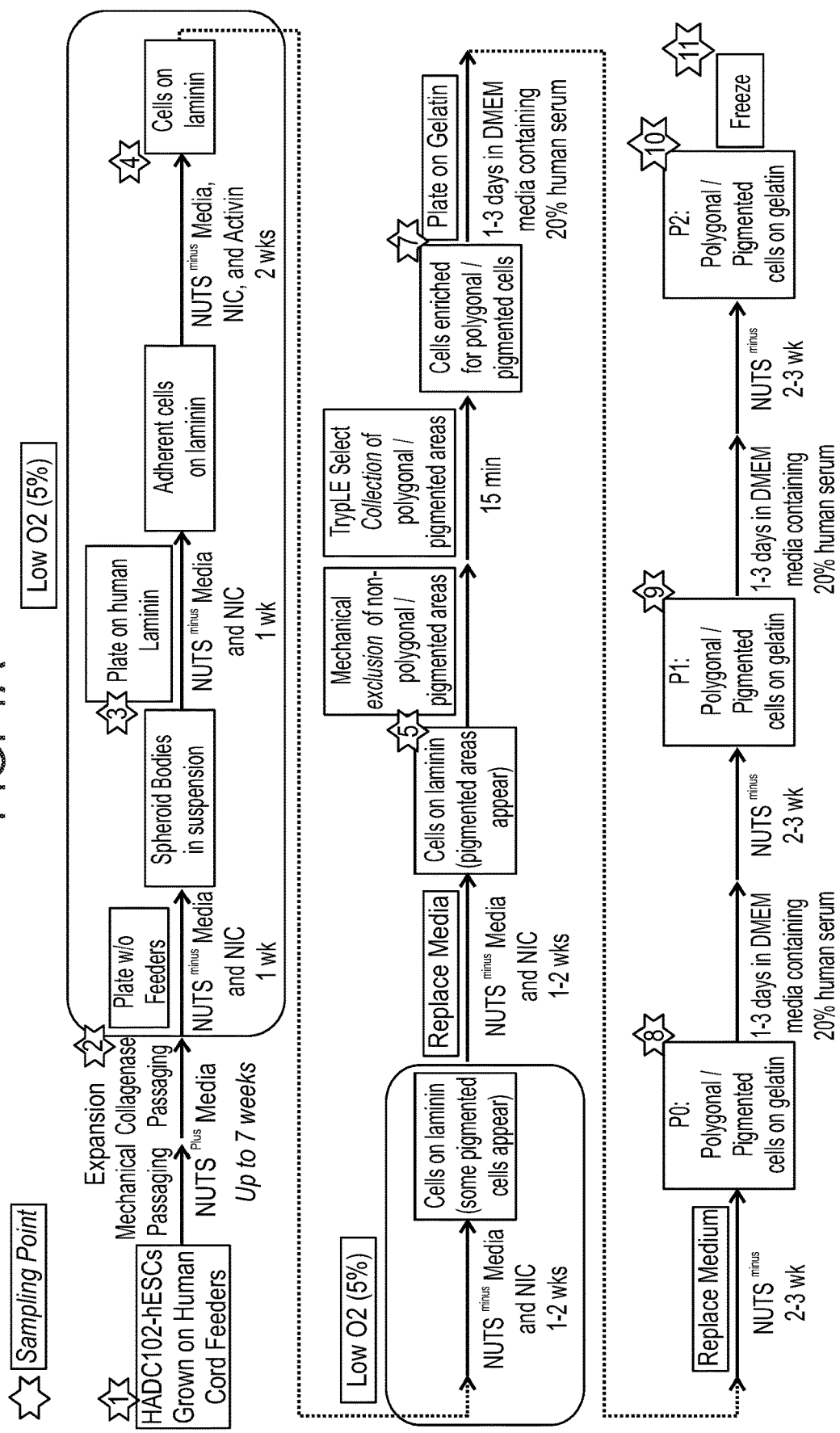
FIGS. 1A-B are outline of the RPE manufacturing process (FIG. 1A) and photoreceptor manufacturing process (FIG. 1B) and in-process control points (yellow stars, In Process Controls, IPCs 1-11). NUTS$^{Plus}$, Nutristem medium containing bFGF and TGFβ; NUTS$^{Minus}$, Nutristem medium w/o bFGF and TGFβ; NIC, Nicotinamide.

The present invention, in some embodiments thereof, relates to methods of preparing photoreceptor cells from pluripotent stem cells.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Human embryonic stem cells have been proposed as a cellular source for the generation of retinal cells including retinal pigment epithelium (RPE) cells and photoreceptors.

U.S. Pat. No. 8,956,866 provides methods for generating RPE cells using a directed differentiation approach using a number of factors including nicotinamide and Activin A.

The present inventors have now shown that using the approach disclosed in U.S. Pat. No. 8,956,866, as well as obtaining RPE cells, it is possible to obtain photoreceptors. Such photoreceptors are useful for the treatment of a myriad of retinal disorders.

Thus, according to a first aspect of the present invention there is provided a method of generating photoreceptors comprising:

(a) culturing a population of human pluripotent stem cells in a medium comprising a differentiating agent to obtain differentiating cells;

(b) culturing the differentiating cells in a culture system comprising a medium which comprises one or more members of the TGFβ superfamily, thereby generating a mixed population of cells comprising retinal pigment epithelial (RPE) cells and photoreceptors;

(c) enriching for the photoreceptors in the mixed population of cells so as to generate a photoreceptor-enriched population of cells; and (d) expanding the photoreceptor-enriched population of cells.

The term "photoreceptors" as used herein refers to biological cells that are capable of phototransduction. The photoreceptors of this aspect of the present invention may be rods and/or cones. Preferably, upon transplantation within an eye, they exhibit functional activities similar to those of native photoreceptors.

According to one embodiment, the photoreceptor cells express at least one, two, three, or four markers of photoreceptor cells. Such markers include, but are not limited to CHX10/VSX2 (visual system homeobox 2), rhodopsin, CRX, Arrestin, Opsin, Recoverin and NRL (neural retina-specific leucine zipper protein).

According to still another embodiment, the photoreceptor cells are capable of treating diseases such as macular degeneration.

"Retinal pigment epithelium cells", "RPE cells", "RPEs", which may be used interchangeably as the context allows, refers to cells of a cell type functionally similar to that of native RPE cells which form the pigment epithelium cell layer of the retina (e.g., upon transplantation within an eye, they exhibit functional activities similar to those of native RPE cells).

According to one embodiment, the RPE cell expresses at least one, two, three, four or five markers of mature RPE cells. Such markers include, but are not limited to CRALBP, RPE65, PEDF, PMEL17, Bestrophin, ZO-1 and tyrosinase. Optionally, the RPE cells may also express a marker of an RPE progenitor—e.g., MITF. In another embodiment, the RPE cells express PAX-6. In another embodiment, the RPE cells express at least one marker of a retinal progenitor cell including, but not limited to Rx, OTX2 or SIX3. Optionally, the RPE cells express either SIX6 and/or LHX2.

As used herein the phrase "markers of mature RPE cells" refers to antigens (e.g., proteins) that are elevated (e.g., at least 2 fold, at least 5 fold, at least 10 fold) in mature RPE cells with respect to non RPE cells or immature RPE cells.

As used herein the phrase "markers of RPE progenitor cells" refers to antigens (e.g., proteins) that are elevated (e.g., at least 2 fold, at least 5 fold, at least 10 fold) in RPE progenitor cells with respect to non RPE cells.

According to another embodiment, the RPE cells have a morphology similar to that of native RPE cells which form the pigment epithelium cell layer of the retina i.e. pigmented and having a characteristic polygonal shape.

According to still another embodiment, the RPE cells are capable of treating diseases such as macular degeneration.

According to still another embodiment, the RPE cells fulfill at least 1, 2, 3, 4 or all of the requirements listed herein above.

As used herein, the phrase "stem cells" refers to cells which are capable of remaining in an undifferentiated state (e.g., pluripotent or multipotent stem cells) for extended periods of time in culture until induced to differentiate into other cell types having a particular, specialized function (e.g., fully differentiated cells). Preferably, the phrase "stem cells" encompasses embryonic stem cells (ESCs), induced pluripotent stem cells (iPSCs), adult stem cells, mesenchymal stem cells and hematopoietic stem cells.

According to a particular embodiment, the photoreceptor cells are generated from pluripotent stem cells (e.g., ESCs or iPSCs).

Induced pluripotent stem cells (iPSCs) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 Feb. 14. (Epub ahead of print); I H Park, Zhao R, West J A, et al., Reprogramming of human somatic cells to pluripotency with defined factors. Nature 2008; 451:141-146; K Takahashi, Tanabe K, Ohnuki M, et al., Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis. In addition, iPSCs may be generated using non-integrating methods e.g., using small molecules or RNA.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG) cells which are obtained from the genital tissue of a fetus any time during gestation, preferably before 10 weeks of gestation. The embryonic stem cells of some embodiments of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by a procedure in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Reubinoff et al., Nat Biotechnol 2000, May: 18(5): 559; Thomson et al., [U.S. Pat. No. 5,843,780; Science 282: 1145, 1998; Curr. Top. Dev. Biol. 38: 133, 1998; Proc. Natl.

Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used according to some embodiments of the invention. Human ES cells can be purchased from the NIH human embryonic stem cells registry [www.grants(dot)nih(dot)gov/stem cells/registry/current(dot)htm] or from other hESC registries. Non-limiting examples of commercially available embryonic stem cell lines are HAD-C102, ESI, BG01, BG02, BG03, BG04, CY12, CY30, CY92, CY10, TE03, TE32, CHB-4, CHB-5, CHB-6, CHB-8, CHB-9, CHB-10, CHB-11, CHB-12, HUES 1, HUES 2, HUES 3, HUES 4, HUES 5, HUES 6, HUES 7, HUES 8, HUES 9, HUES 10, HUES 11, HUES 12, HUES 13, HUES 14, HUES 15, HUES 16, HUES 17, HUES 18, HUES 19, HUES 20, HUES 21, HUES 22, HUES 23, HUES 24, HUES 25, HUES 26, HUES 27, HUES 28, CyT49, RUES3, WA01, UCSF4, NYUES1, NYUES2, NYUES3, NYUES4, NYUES5, NYUES6, NYUES7, UCLA 1, UCLA 2, UCLA 3, WA077 (H7), WA09 (H9), WA13 (H13), WA14 (H14), HUES 62, HUES 63, HUES 64, CT1, CT2, CT3, CT4, MA135, Eneavour-2, WIBR1, WIBR3, WIBR4, WIBR5, WIBR6, HUES 45, Shef 3, Shef 6, BJNhem19, BJNhem20, SA001.

According to a specific embodiment, the embryonic stem cell line is HAD-C102 or ESI.

In addition, ES cells can be obtained from other species as well, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al., 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, Mo., USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

Another method for preparing ES cells is described in Chung et al., Cell Stem Cell, Volume 2, Issue 2, 113-117, 7 Feb. 2008. This method comprises removing a single cell from an embryo during an in vitro fertilization process. The embryo is not destroyed in this process.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

Yet another method for preparing ES cells is by parthenogenesis. The embryo is also not destroyed in the process.

Currently practiced ES culturing methods are mainly based on the use of feeder cell layers which secrete factors needed for stem cell proliferation, while at the same time, inhibit their differentiation. The culturing is typically effected on a solid surface—e.g., a surface coated with gelatin or vimentin. Exemplary feeder layers include Human embryonic fibroblasts, adult fallopian epithelial cells, primary mouse embryonic fibroblasts (PMEF), mouse embryonic fibroblasts (MEF), murine fetal fibroblasts (MFF), human embryonic fibroblast (HEF), human fibroblasts obtained from the differentiation of human embryonic stem cells, human fetal muscle cells (HFM), human fetal skin cells (HFS), human adult skin cells, human foreskin fibroblasts (HFF), human umbilical cord fibroblasts, human cells obtained from the umbilical cord or placenta, and human marrow stromal cells (hMSCs). Growth factors may be added to the medium to maintain the ESCs in an undifferentiated state. Such growth factors include bFGF and/or TGFβ. In another embodiment, agents may be added to the medium to maintain the hESCs in a naïve undifferentiated state—see for example Kalkan et al., 2014, Phil. Trans. R. Soc. B, 369: 20130540.

Human cord feeder-layer—Human cord fibroblasts may be expanded in Dulbecco's Modified Eagle's Medium (e.g., DMEM, SH30081.01, Hyclone) supplemented with human serum (e.g., 20%) and glutamine. Preferably the human cord cells are irradiated. This may be effected using methods known in the art (e.g., Gamma cell, 220 Exel, MDS Nordion 3,500 rads). Once sufficient cells are obtained they may be frozen (e.g., cryopreserved). For expansion of ESCs, the human cord fibroblasts are typically seeded on a solid surface (e.g., T75 or T175 flasks) optionally coated with an adherent substrate such as gelatin (e.g., recombinant human gelatin (RhG100-001, Fibrogen) at a concentration of 25-40,000 cells/cm$^2$ in DMEM (e.g., SH30081.01, Hyclone) supplemented with about 20% human serum (and glutamine). hESCs are typically plated on top of the feeder cells 1-4 days later in a supportive medium (e.g., Nutristem with human serum albumin). Additional factors may be added to the medium to prevent differentiation of the ESCs such as bFGF and TGF-β. Once a sufficient amount of hESCs are obtained, the cells may be mechanically disrupted (e.g., by using a sterile tip or a disposable sterile stem cell tool; 14602 Swemed). Alternatively, the cells may be removed by enzymatic treatment (e.g., collagenase A, or TrypLE Select) or chemical treatment (e.g., EDTA). This process may be repeated several times to reach the necessary amount of hESC. According to a particular embodiment, following the first round of expansion, the hESCs are removed using TrypLE Select and following the second round of expansion, the hESCs are removed using collagenase A.

Human embryonic fibroblasts or adult fallopian epithelial cells as feeder cell layers—Human ES cells can be grown and maintained using human embryonic fibroblasts or adult fallopian epithelial cells. When grown on these human feeder cells the human ES cells exhibit normal karyotypes, present alkaline phosphatase activity, express Oct-4 and other embryonic cell surface markers including SSEA-3, SSEA-4, TRA-1-60, and GCTM-2, form teratomas in vivo, and retain all key morphological characteristics [Richards M, Fong C Y, Chan W K, Wong P C, Bongso A. (2002). Human feeders support prolonged undifferentiated growth of human inner cell masses and embryonic stem cells. Nat. Biotechnol. 20: 933-6].

Foreskin feeder layer—Human ES cells can be cultured on human foreskin feeder layer as disclosed in U.S. patent application Ser. No. 10/368,045. Foreskin derived feeder cell layers consist of a complete animal-free environment suitable for culturing human ES cells. In addition, foreskin cells can be maintained in culture for as long as 42 passages since their derivation, providing the ES cells with a relatively constant environment. Under these conditions the human ES cells were found to be functionally indistinct from cells grown with alternate protocols (e.g., MEF). Following differentiation, ES cells expressed genes associated with all three embryonal germ layers, in vitro, and formed teratomas in vivo, consisting of tissue arising from all three germ layers.

Feeder cell free systems have also been used in ES cell culturing, such systems utilize matrices supplemented with serum replacement, cytokines and growth factors (including IL6 and soluble IL6 receptor chimera) as a replacement for the feeder cell layer. Stem cells can be grown on a solid surface such as an extracellular matrix (e.g., Matrigel® or laminin) in the presence of a culture medium—for example the Lonza L7 system, mTeSR, StemPro, XFKSR, E8). Unlike feeder-based cultures which require the simultaneous growth of feeder cells and stem cells and which may result in mixed cell populations, stem cells grown on feeder-free systems are easily separated from the surface.

The ESCs may be expanded on feeders prior to the differentiation step. Exemplary feeder-layer based cultures contemplated by the present invention are described herein above. The expansion is typically effected for at least two days, three days, four days, five days, six days or seven days. The expansion is effected for at least 1 passage, or at least 2, at least 3, at least 4, at least 5, at least 6, at least 7, at least 8, at least 9 or at least 10 passages.

Following expansion, the pluripotent stem cells (e.g., ESCs) are subjected to directed differentiation using a differentiating agent.

In one exemplary differentiation protocol, the embryonic stem cells are differentiated towards the retinal cell lineage using a first differentiating agent and then further differentiated towards photoreceptor cells using a member of the transforming growth factor-ß (TGFß) superfamily, (e.g., TGFβ1, TGFβ2, and TGFβ3 subtypes, as well as homologous ligands including activin (e.g., activin A, activin B, and activin AB), nodal, anti-mullerian hormone (AMH), some bone morphogenetic proteins (BMP), e.g., BMP2, BMP3, BMP4, BMP5, BMP6, and BMP7, and growth and differentiation factors (GDF)). According to a specific embodiment, the member of the transforming growth factor-ß (TGFß) superfamily is activin A—e.g., 0.01-1000 ng/ml, 0.1-200 ng/ml, 1-200 ng/ml—for example 140 ng/ml, 150 ng/ml, 160 ng/ml or 180 ng/ml).

Thus activin A may be added at a final molarity of 0.1 pM-10 nM, 10 pM-10 nM, 0.1 nM-10 nM, 1 nM-10 nM, for example 5.4 nM. According to a particular embodiment, the first differentiating agent is nicotinamide (NA)—e.g. between 0.01-100 mM, 0.1-100 mM, 0.1-50 mM, 5-50 mM, 5-20 mM, e.g. 10 mM.

According to another embodiment, the first differentiating agent is 3-aminobenzamide.

NA, also known as "niacinamide", is the amide derivative form of Vitamin B3 (niacin) which is thought to preserve and improve beta cell function. NA has the chemical formula $C_6H_6N_2O$. NA is essential for growth and the conversion of foods to energy, and it has been used in arthritis treatment and diabetes treatment and prevention.

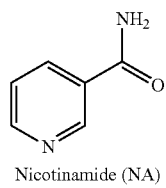

Nicotinamide (NA)

According to a particular embodiment, the nicotinamide is a nicotinamide derivative or a nicotinamide mimic. The term "derivative of nicotinamide (NA)" as used herein denotes a compound which is a chemically modified derivative of the natural NA. In one embodiment, the chemical modification may be a substitution of the pyridine ring of the basic NA structure (via the carbon or nitrogen member of the ring), via the nitrogen or the oxygen atoms of the amide moiety. When substituted, one or more hydrogen atoms may be replaced by a substituent and/or a substituent may be attached to a N atom to form a tetravalent positively charged nitrogen. Thus, the nicotinamide of the present invention includes a substituted or non-substituted nicotinamide. In another embodiment, the chemical modification may be a deletion or replacement of a single group, e.g., to form a thiobenzamide analog of NA, all of which being as appreciated by those versed in organic chemistry. The derivative in the context of the invention also includes the nucleoside derivative of NA (e.g., nicotinamide adenine). A variety of derivatives of NA are described, some also in connection with an inhibitory activity of the PDE4 enzyme (WO03/068233; WO02/060875; GB2327675A), or as VEGF-receptor tyrosine kinase inhibitors (WO01/55114). For example, the process of preparing 4-aryl-nicotinamide derivatives (WO05/014549). Other exemplary nicotinamide derivatives are disclosed in WO01/55114 and EP2128244.

Nicotinamide mimics include modified forms of nicotinamide, and chemical analogs of nicotinamide which recapitulate the effects of nicotinamide in the differentiation and maturation of RPE cells from pluripotent cells. Exemplary nicotinamide mimics include benzoic acid, 3-aminobenzoic acid, and 6-aminonicotinamide. Another class of compounds that may act as nicotinamide mimics are inhibitors of poly(ADP-ribose) polymerase (PARP). Exemplary PARP inhibitors include 3-aminobenzamide, Iniparib (BSI 201), Olaparib (AZD-2281), Rucaparib (AG014699, PF-01367338), Veliparib (ABT-888), CEP 9722, MK 4827, and BMN-673.

Additional contemplated differentiation agents include for example noggin, antagonists of FGF, (Dkk1 or IWR1e), nodal antagonists (Lefty-A), retinoic acid, taurine, GSK3b inhibitor (CHIR99021), notch inhibitor (DAPT), retinoic acid receptor (RAR) agonists or antagonists, agonists of FGF signaling pathway (aFGF, bFGF), agonists of the Hedgehog pathway (Shh), agonists of insulin growth factor pathway (IGF), agonists of the PI3-Kinase pathway, EGF pathway, BMP pathway, and Hippo pathway.

Such differentiation agents may be added at any stage of the differentiation procedure—e.g. prior to the first differentiation step, during the first differentiation step, during the second differentiation step or following the second differentiation step.

According to a particular embodiment, the differentiation is effected as follows:

a) culture of ESCs in a medium comprising a first differentiating agent (e.g., nicotinamide). This step may be effected for a minimum of one day, two days, three days, 4 days, 5 days, 6 days, 1 week, 10 days, 2 weeks, three weeks, four weeks, five weeks or even 6 weeks.

b) culture of cells obtained from step a) in a medium comprising a member of the TGFß superfamily (e.g., activin A) and optionally together with the first differentiating agent (e.g., nicotinamide). This step may be effected for a minimum of one day, two days, three days, 4 days, 5 days, 6 days, 1 week, 10 days, 2 weeks, three weeks, four weeks, five weeks or even 6 weeks.

Preferably, step (a) is effected in the absence of the member of the TGFß superfamily (e.g., activin A),In one embodiment, the medium is completely devoid of a member of the TGFß superfamily (e.g., activin A). In another embodiment, the level of TGFß superfamily member in the medium is less than 20 ng/ml, 10 ng/ml, 1 ng/ml or even less than 0.1 ng/ml.

The above described protocol may be continued by culturing the cells obtained in step b) in a medium comprising the first differentiating agent (e.g., nicotinamide), but devoid of a member of the TGFß superfamily (e.g., activin A). This step is referred to herein as step (b*).

The above described protocol is now described in further detail, with additional embodiments.

Step (a): The differentiation process is started once sufficient quantities of ESCs are obtained. They are typically removed from the cell culture (e.g., by using collagenase A, dispase, TrypLE select, EDTA) and plated onto a non-adherent substrate (e.g., cell culture plate such as Hydrocell or an agarose-coated culture dish, or petri bacteriological dishes) in the presence of nicotinamide (and the absence of activin A). Exemplary concentrations of nicotinamide are between 0.01-100 mM, 0.1-100 mM, 0.1-50 mM, 5-50 mM, 5-20 mM, e.g. 10 mM. Once the cells are plated onto the non-adherent substrate (e.g., cell culture plate), the cell culture may be referred to as a cell suspension, preferably free floating clusters in a suspension culture, i.e. aggregates of cells derived from human embryonic stem cells (hESCs). The cell clusters do not adhere to any substrate (e.g., culture plate, carrier). Sources of free floating stem cells were previously described in WO 06/070370, which is herein incorporated by reference in its entirety. This stage may be effected for a minimum of 1 day, more preferably two days, three days, 1 week or even 14 days. Preferably, the cells are not cultured for more than 3 weeks in suspension together with the nicotinamide e.g., between 0.01-100 mM, 0.1-100 mM, 0.1-50 mM, 5-50 mM, 5-20 mM, e.g. 10 mM (and in the absence of activin A). In one embodiment, the cells are cultured for 6-8 days in suspension together with the nicotinamide e.g. between 0.01-100 mM, 0.1-100 mM, 0.1-50 mM, 5-50 mM, 5-20 mM, e.g. 10 mM (and in the absence of activin A.

According to one embodiment, when the cells are cultured on the non-adherent substrate e.g., cell culture plates, the atmospheric oxygen conditions are 20%. However, manipulation of the atmospheric oxygen conditions is also contemplated such that the atmospheric oxygen percent is less than about 20%, 15%, 10%, 9%, 8%, 7%, 6% or even less than about 5% (e.g., between 1%-20%, 1%-10% or 0-5%).

According to a particular embodiment, the cells are cultured on the non-adherent substrate initially under normal atmospheric oxygen conditions and then lowered to less than normal atmospheric oxygen conditions.

Examples of non-adherent cell culture plates include those manufactured by Nunc (e.g., Hydrocell; Cat No. 174912).

Typically, the clusters comprise at least 50-500,000, 50-100,000, 50-50,000, 50-10,000, 50-5000, 50-1000 cells. According to one embodiment, the cells in the clusters are not organized into layers and form irregular shapes. In one embodiment, the clusters are devoid of pluripotent embryonic stem cells. In another embodiment, the clusters comprise small amounts of pluripotent embryonic stem cells (e.g., no more than 5%, or no more than 3% (e.g., 0.01-2.7%) cells that co-express OCT4 and TRA 1-60 at the protein level). Typically, the clusters comprise cells that have been partially differentiated under the influence of nicotinamide. Such cells primarily express neural and retinal precursor markers such as PAX6, Rax, Six3 and/or CHX10.

The clusters may be dissociated using enzymatic or non-enzymatic methods (e.g., mechanical, chemical) known in the art. According to one embodiment, the cells are dissociated such that they are no longer in clusters—e.g., aggregates or clumps of 2-100,000 cells, 2-50,000 cells, 2-10,000 cells, 2-5000 cells, 2-1000 cells, 2-500 cells, 2-100 cells, 2-50 cells. According to a particular embodiment, the cells are in a single cell suspension.

The cells (e.g., dissociated cells) are then plated on an adherent substrate and cultured in the presence of nicotinamide e.g., e.g. between 0.01-100 mM, 0.1-100 mM, 0.1-50 mM, 5-50 mM, 5-20 mM, e.g. 10 mM (and the absence of activin A). This stage may be effected for a minimum of 1 day, more preferably two days, three days, 1 week or even 14 days. Preferably, the cells are not cultured for more than 3 weeks in the presence of nicotinamide (and in the absence of activin). In an exemplary embodiment, this stage is effected for 6-7 days.

According to one embodiment, when the cells are cultured on the adherent substrate e.g., laminin, the atmospheric oxygen conditions are 20%. They may be manipulated such that the percentage is less than about 20%, 15%, 10%, more preferably less than about 9%, less than about 8%, less than about 7%, less than about 6% and more preferably about 5% (e.g., between 1%-20%, 1% -10% or 0-5%).

According to a particular embodiment, the cells are cultured on the adherent substrate initially under normal atmospheric oxygen conditions and then lowered to less than normal atmospheric oxygen conditions.

Examples of adherent substrates include but are not limited to fibronectin, laminin, polyD-lysine, collagen and gelatin.

Step (b): Following the first stage of directed differentiation, (step a; i.e. culture in the presence of nicotinamide (e.g. between 0.01-100 mM, 0.1-100 mM, 0.1-50 mM, 5-50 mM, 5-20 mM, e.g. 10 mM), the semi-differentiated cells are then subjected to a further stage of differentiation on an adherent substrate—culturing in the presence of activin A (e.g., 100-200 ng/ml—for example 140 ng/ml, 150 ng/ml, 160 ng/ml or 180 ng/ml). Nicotinamide may be added at this stage (e.g. between 0.01-100 mM, 0.1-100 mM, 0.1-50 mM, 5-50 mM, 5-20 mM, e.g. 10 mM). This stage may be effected for 1 day to 10 weeks, 3 days to 10 weeks, 1 week to 10 weeks, one week to eight weeks, one week to four weeks, for example for at least one day, at least two days, at least three days, at least 5 days, at least one week, at least two weeks, at least three weeks, at least four weeks, at least five weeks, at least six weeks, at least seven weeks, at least eight weeks, at least nine weeks, at least ten weeks.

According to a specific embodiment, this stage is effected for about two weeks. This stage of differentiation may be effected at low or normal atmospheric oxygen conditions, as detailed herein above.

Step (b*): Following the second stage of directed differentiation (i.e. culture in the presence of nicotinamide and activin A on an adherent substrate; step (b)), the further differentiated cells are optionally subjected to a subsequent stage of differentiation on the adherent substrate—culturing in the presence of nicotinamide (e.g. between 0.01-100 mM, 0.1-100 mM, 0.1-50 mM, 5-50 mM, 5-20 mM, e.g. 10 mM), in the absence of activin A. This stage may be effected for at least one day, 2, days, 5 days, at least one week, at least two weeks, at least three weeks or even four weeks. Preferably this stage is effected for about one week. This stage of differentiation may also be carried out at low or normal atmospheric oxygen conditions, as detailed herein above.

The basic medium in which the ESCs are differentiated is any known cell culture medium known in the art for supporting cells growth in vitro, typically, a medium comprising a defined base solution, which includes salts, sugars, amino acids and any other nutrients required for the maintenance of the cells in the culture in a viable state. According to a specific embodiment, the basic medium is not a conditioned medium. Non-limiting examples of commercially available basic media that may be utilized in accordance with the invention comprise Nutristem (without bFGF and TGFβ for ESC differentiation, with bFGF and TGFβ for ESC expansion) Neurobasal™, KO-DMEM, DMEM, DMEM/F12, Cellgro™ Stem Cell Growth Medium, or X-Vivo™. The basic medium may be supplemented with a variety of agents as known in the art dealing with cell cultures. The following is a non-limiting reference to various supplements that may be included in the culture system to be used in accordance with the present disclosure:

- serum or with a serum replacement containing medium, such as, without being limited thereto, knock out serum replacement (KOSR), Nutridoma-CS, TCH™, N2, N2 derivative, or B27 or a combination;
- an extracellular matrix (ECM) component, such as, without being limited thereto, fibronectin, laminin, collagen and gelatin. The ECM may then be used to carry the one or more members of the TGFß superfamily of growth factors;
- an antibacterial agent, such as, without being limited thereto, penicillin and streptomycin;
- non-essential amino acids (NEAA);
- neurotrophins which are known to play a role in promoting the survival of SCs in culture, such as, without being limited thereto, BDNF, NT3, NT4.

According to a preferred embodiment, the medium used for differentiating the ESCs is Nutristem medium (Biological Industries, 06-5102-01-1A).

According to a particular embodiment differentiation and expansion of ESCs is effected under xeno free conditions.

According to one embodiment, the proliferation/growth medium is devoid of xeno contaminants i.e. free of animal derived components such as serum, animal derived growth factors and albumin. Thus, according to this embodiment, the culturing is performed in the absence of xeno contaminants.

Other methods for culturing ESCs under xeno free conditions are provided in U.S. Patent Application No. 20130196369, the contents of which are incorporated in their entirety.

The preparations comprising photoreceptor cells may be prepared in accordance with Good Manufacturing Practices (GMP) (e.g., the preparations are GMP-compliant) and/or current Good Tissue Practices (GTP) (e.g., the preparations may be GTP-compliant).

During differentiation steps, the embryonic stem cells may be monitored for their differentiation state. Cell differentiation can be determined upon examination of cell or tissue-specific markers which are known to be indicative of differentiation.

Tissue/cell specific markers can be detected using immunological techniques well known in the art [Thomson J A et al., (1998). Science 282: 1145-7]. Examples include, but are not limited to, flow cytometry for membrane-bound or intracellular markers, immunohistochemistry for extracellular and intracellular markers and enzymatic immunoassay, for secreted molecular markers.

Following the stages of differentiation described herein above, a mixed cell population is obtained comprising both polygonal/pigmented and non-polygonal/non-pigmented cells (i.e. photoreceptors). According to one embodiment, at least 10%, 20%, 30%, 40%, 50%, 60%, 70%, 80% or even 90% of the cells of the mixed population are non-pigmented (i.e. photoreceptors).

In the next step of the process the non-pigmented cells (i.e. photoreceptors) are isolated (e.g., separated) or enriched from the RPE cells (pigmented cells) to generate an enriched population of photoreceptors.

According to one embodiment, the photoreceptors are enriched by mechanical selection or by use of surface markers.

According to this aspect of the present invention, at least 10%, 20%, 30%, 40%, 50%, 60%, 70%, at least 80%, at least 90%, at least 95%, or even 100% of the cells which are removed from the culture system (and subsequently expanded) are non-pigmented cells.

According to this aspect of the present invention, at least 30%, 40% 50%, 60%, 70%, 80%, 90% of all the cells in the culture system are removed (and subsequently expanded).

According to one embodiment, less than 90% of the cells that are removed (and subsequently cultured) are pigmented cells. According to another embodiment, less than 80% of the cells that are removed (and subsequently cultured) are pigmented cells. According to another embodiment, less than 70% of the cells that are removed (and subsequently cultured) are pigmented cells. According to another embodiment, less than 60% of the cells that are removed (and subsequently cultured) are pigmented cells. According to another embodiment, less than 50% of the cells that are removed (and subsequently cultured) are pigmented cells. According to another embodiment, less than 40% of the cells that are removed (and subsequently cultured) are pigmented cells. According to another embodiment, less than 30% of the cells that are removed (and subsequently cultured) are pigmented cells. According to another embodiment, less than 20% of the cells that are removed (and subsequently cultured) are pigmented cells. According to another embodiment, less than 10% of the cells that are removed (and subsequently cultured) are pigmented cells. According to another embodiment, less than 5% of the cells that are removed (and subsequently cultured) are pigmented cells. According to another embodiment, less than 2% of the cells that are removed (and subsequently cultured) are pigmented cells. According to another embodiment, less than 1% of the cells that are removed (and subsequently cultured) are pigmented cells.

The present inventor has shown that cells removed from the culture system following the differentiation process described herein express markers of photoreceptors. Such cells may be used to treat retinal disorders.

Optionally, the photoreceptors may be cultured so as to obtain greater numbers of photoreceptor cells (i.e.

expanded). Care should be taken during the expansion phase that conditions therein do not promote expansion of RPE cells over photoreceptor cells. In one embodiment, the culturing enriches for the photoreceptor cells. Thus, for example, in one embodiment, no more than 5%, 10%, 15%, 20% of the cells which are expanded are RPE cells. According to another embodiment between 5-90% of the cells which are expanded are RPE cells. According to another embodiment between 5-80% of the cells which are expanded are RPE cells. According to another embodiment between 5-70% of the cells which are expanded are RPE cells. According to another embodiment between 5-60% of the cells which are expanded are RPE cells. According to another embodiment between 5-50% of the cells which are expanded are RPE cells. According to another embodiment, between 10-50% of the cells which are expanded are RPE cells. According to another embodiment, between 20-50% of the cells which are expanded are RPE cells. According to another embodiment, between 30-50% of the cells which are expanded are RPE cells. According to another embodiment, between 10-40% of the cells which are expanded are RPE cells. According to another embodiment, between 10-30% of the cells which are expanded are RPE cells. According to another embodiment, between 10-20% of the cells which are expanded are RPE cells.

Expansion of the enriched population of cells comprising photoreceptors may be effected on an extra cellular matrix, e.g., gelatin, collagen I, collagen IV, laminin (e.g., laminin 521), fibronectin or poly-D-lysine.

The photoreceptors may be cultured in agents known to further promote the differentiation and or survival of photoreceptors. Such agents include, but are not limited to FGF, shh, noggin, antagonists of Wnt (Dkk1 or IWR1e), nodal antagonists (Lefty-A), retinoic acid, taurine, GSK3b inhibitor (CHIR99021) and notch inhibitor (DAPT).

In one embodiment, the expanding is effected in the presence of nicotinamide (e.g. between 0.01-100 mM, 0.1-100 mM, 0.1-50 mM, 5-50 mM, 5-20 mM, e.g. 10 mM), and in the absence of activin A.

The enriched population of photoreceptor cells may be expanded in suspension (with or without a micro-carrier) or in a monolayer. The expansion of the enriched population of photoreceptor cells in monolayer cultures or in suspension culture may be modified to large scale expansion in bioreactors or multi/hyper stacks by methods well known to those versed in the art.

According to one embodiment, the expansion phase is effected for at least one week, at least 2 weeks, at least 3 weeks, at least 4 weeks, at least 5 weeks, at least 6 weeks, at least 7 weeks, at least 8 weeks, at least 9 weeks or even 10 weeks. Preferably, the expansion phase is effected for 1 week-10 weeks, more preferably 2 weeks-10 weeks, more preferably, 3 weeks-10 weeks, more preferably 4 weeks-10 weeks, or 4 weeks-8 weeks.

According to still another embodiment, the enriched population of photoreceptor cells are passaged at least 1 time during the expansion phase, at least twice during the expansion phase, at least three times during the expansion phase, at least four times during the expansion phase or at least five times during the expansion phase or at least six times during the expansion phase.

The population of photoreceptor cells generated according to the methods described herein may be characterized according to a number of different parameters.

Thus, for example, the photoreceptor cells obtained may be with an elongated cell body and an apex of cytoplasm.

Harvesting of the expanded population of photoreceptor cells may be effected using methods known in the art (e.g., using an enzyme such as trypsin, EDTA).

Following harvesting, the populations of photoreceptors cells may optionally be cryopreserved using methods known in the art. Examples of media suitable for cryopreservation include but are not limited to 90% Human Serum/10% DMSO, CryoStor® 10%, 5% and 2%, Stem Cellbanker® and Prime XV® FreezIS.

It will be appreciated that the cell populations disclosed herein are devoid of undifferentiated human embryonic stem cells. According to one embodiment, less than 1:250,000 cells are Oct4$^+$TRA-1-60$^+$ cells, as measured for example by FACS. The cells also have down-regulated (by more than 5,000 fold) expression of GDF3 or TDGF as measured by PCR.

The photoreceptor cells of this aspect of the present invention do not express embryonic stem cell markers. Said one or more embryonic stem cell markers may be OCT-4, NANOG, SSEA-3, SSEA-4, TRA-1-60, and/or TRA-1-81.

The photoreceptor preparations may be substantially enriched, with respect to non-photoreceptor cells, comprising at least about 75%, 80%, 85%, 90%, 91%, 92%, 93%, 94%, 95%, 96%, 97%, 98%, 99%, or 100% photoreceptor cells. The photoreceptor cell preparation may be essentially free of RPE cells or consist of photoreceptor cells. For example, the substantially enriched preparation of photoreceptor cells may comprise less than about 25%, 20%, 15%, 10%, 9%, 8%, 7%, 6%, 5%, 4%, 3%, 2%, or 1% non-photoreceptor cell type, for example RPE cells. For example, the photoreceptor cell preparation may comprise less than about 25%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% non-photoreceptor cells, for example RPE cells.

The preparations described herein may be substantially free of bacterial, viral, or fungal contamination or infection, including but not limited to the presence of HIV I, HIV 2, HBV, HCV, HAV, CMV, HTLV 1, HTLV 2, parvovirus B19, Epstein-Barr virus, or herpesvirus 1 and 2, SV40, HHV5, 6, 7, 8, CMV, polyoma virus, HPV, Enterovirus. The preparations described herein may be substantially free of mycoplasma contamination or infection.

Another way of characterizing the cell populations disclosed herein is by marker expression. Thus, for example, at least 70%, 80%, 85%, 90%, 95% or 100% of the cells express RAX, as measured by immunostaining. According to one embodiment, between 70-100% of the cells express RAX. Preferably, the level of RAX expressed by the cells of the present invention is at least 2 fold greater, 5 fold greater or even 10 fold greater than the level of expression in RPE cells or non-differentiated ESCs, as measured by RT-PCR.

According to another embodiment, at least 70%, 80%, 85%, 87%, 89%, 90%, 95%, 97% or 100% of the cells express CHX10, as measured by immunostaining. For example, between 70-100% of the cells express CHX10. Preferably, the level of CHX10 expressed by the cells of the present invention is at least 2 fold greater, 5 fold greater or even 10 fold greater than the level of expression in RPE cells or non-differentiated ESCs, as measured by RT-PCR.

According to another embodiment, at least 70%, 80%, 85%, 87%, 89%, 90%, 95%, 97% or 100% of the cells express rhodopsin, as measured by immunostaining. Preferably, the level of rhodopsin expressed by the cells of the present invention is at least 2 fold greater, 5 fold greater or even 10 fold greater than the level of expression in RPE cells or non-differentiated ESCs, as measured by RT-PCR.

According to another embodiment, at least 70%, 80%, 85%, 87%, 89%, 90%, 95%, 97% or 100% of the cells express neural retina-specific leucine zipper protein (NRL), as measured by immunostaining. For example, between 70-100% of the cells express by immunostaining. Preferably, the level of NRL expressed by the cells of the present invention is at least 2 fold greater, 5 fold greater or even 10 fold greater than the level of expression in RPE cells or non-differentiated ESCs, as measured by RT-PCR.

Preferably, the cells of this aspect of the present invention do not express markers of RPE cells. Thus, for example, preferably the cells of the present invention do not express (or less than 30%, 25%, 20%, 15%, 10% of the cells express) MITF, RPE65, bestrophin 1, premelanosome protein (PMEL17) or CRALBP. Preferably, the level of RPE markers expressed by the cells of the present invention is at least 2 fold less, 5 fold less or even 10 fold less than the level of expression in RPE cells, as measured by RT-PCR.

It would be well appreciated by those versed in the art that the derivation of photoreceptor cells is of great benefit. They may be used as an in vitro model for the development of new drugs to promote their survival, regeneration and function. Photoreceptor cells may serve for high throughput screening for compounds that have a toxic or regenerative effect on photoreceptor cells. They may be used to uncover mechanisms, new genes, soluble or membrane-bound factors that are important for the development, differentiation, maintenance, survival and function of photoreceptor cells.

The photoreceptor cells may also serve as an unlimited source of photoreceptor cells for transplantation, replenishment and support of malfunctioning or degenerated photoreceptor cells in retinal degenerations. Furthermore, genetically modified photoreceptor cells may serve as a vector to carry and express genes in the eye and retina after transplantation.

Eye conditions for which the photoreceptor cells may serve as therapeutics include, but are not limited to retinal diseases or disorders generally associated with retinal dysfunction, retinal injury, and/or loss of photoreceptor function. A non-limiting list of conditions which may be treated in accordance with the invention comprises retinitis pigmentosa, lebers congenital amaurosis, hereditary or acquired macular degeneration, age related macular degeneration (AMD), dry AMD, Best disease, retinal detachment, gyrate atrophy, choroideremia, pattern dystrophy as well as other dystrophies of the RPE, Stargardt disease, RPE and retinal damage due to damage caused by any one of photic, laser, inflammatory, infectious, radiation, neo vascular or traumatic injury.

The present inventors further contemplate use of the photoreceptor cells for treatment of other diseases such as neurodegenerative diseases including but not limited to Parkinson's, ALS, Multiple Sclerosis, Huntingdon's disease, autoimmune encephalomyelitis, diabetic neuropathy, Alzheimer's and epilepsy.

Subjects which may be treated include primate (including humans), canine, feline, ungulate (e.g., equine, bovine, swine (e.g., pig)), avian, and other subjects. Humans and non-human animals having commercial importance (e.g., livestock and domesticated animals) are of particular interest. Exemplary mammals which may be treated include, canines; felines; equines; bovines; ovines; rodentia, etc. and primates, particularly humans. Non-human animal models, particularly mammals, e.g., primate, murine, lagomorpha, etc. may be used for experimental investigations.

The photoreceptor cells generated as described herein may be transplanted to various target sites within a subject's eye. In accordance with one embodiment, the transplantation of the photoreceptor cells is to the subretinal space of the eye. In addition, dependent upon migratory ability and/or positive paracrine effects of the cells, transplantation into additional ocular compartments can be considered including the vitreal space, inner or outer retina, the retinal periphery and within the choroids.

The numbers of viable cells that may be administered to the subject are typically between $5000\text{-}10\times10^6$ per injection, e.g. between $50,000\text{-}5\times10^6$ per injection.

The cells are typically formulated in a carrier (e.g., an isotonic solution and/or a saline) such as BSS plus™. Other contemplated solutions include cryopreservation solutions such as Cryostor® 5 or Cryostor® 2. The carrier may optionally comprise additional factors that support RPE engraftment, integration, survival, potency etc.

The transplantation may be performed by various techniques known in the art. Methods for performing retinal cell transplants are described in, for example, U.S. Pat. Nos. 5,962,027, 6,045,791, and 5,941,250 and in Eye Graefes Arch Clin Exp Opthalmol March 1997; 235(3):149-58; Biochem Biophys Res Commun Feb. 24, 2000; 268(3): 842-6; Opthalmic Surg February 1991; 22(2): 102-8. Methods for performing corneal transplants are described in, for example, U.S. Pat. No. 5,755,785, and in Eye 1995; 9 (Pt 6 Su):6-12; Curr Opin Opthalmol August 1992; 3 (4): 473-81; Ophthalmic Surg Lasers April 1998; 29 (4): 305-8; Ophthalmology April 2000; 107 (4): 719-24; and Jpn J Ophthalmol November-December 1999; 43(6): 502-8. If mainly paracrine effects are to be utilized, cells may also be delivered and maintained in the eye encapsulated within a semi-permeable container, which will also decrease exposure of the cells to the host immune system (Neurotech USA CNTF delivery system; PNAS Mar. 7, 2006 vol. 103(10) 3896-3901).

The step of administering may comprise intraocular administration of the photoreceptor cells into an eye in need thereof. The intraocular administration may comprise injection of the photoreceptor cells into the subretinal space.

In accordance with one embodiment, transplantation is performed via pars plane vitrectomy surgery followed by delivery of the cells through a small retinal opening into the sub-retinal space or by direct injection.

The photoreceptor cells may be transplanted in various forms. For example, the photoreceptor cells may be introduced into the target site in the form of single cell suspension, with matrix or adhered onto a matrix or a membrane, extracellular matrix or substrate such as a biodegradable polymer or a combination. The photoreceptor cells may also be transplanted together (co-transplantation) with other retinal cells, such as with RPE cells.

The effectiveness of treatment may be assessed by different measures of visual and ocular function and structure, including, among others, best corrected visual acuity (BCVA), retinal sensitivity to light as measured by perimetry or microperimetry in the dark and light-adapted states, full-field, multi-focal, focal or pattern electroretinography ERG), contrast sensitivity, reading speed, color vision, clinical biomicroscopic examination, fundus photography, optical coherence tomography (OCT), fundus auto-fluorescence (FAF), infrared and multicolor imaging, fluorescein or ICG angiography, adoptive optics and additional means used to evaluate visual function and ocular structure.

The subject may be administered corticosteroids prior to or concurrently with the administration of the photoreceptor cells, such as prednisolone or methylprednisolone, Predforte.

According to another embodiment, the subject is not administered corticosteroids prior to or concurrently with the administration of the photoreceptor cells, such as prednisolone or methylprednisolone, Predforte.

Immunosuppressive drugs may be administered to the subject prior to, concurrently with and/or following treatment.

The immunosuppressive drug may belong to the following classes:

Glucocorticoids, Cytostatics (e.g., alkylating agent or antimetabolite), antibodies (polyclonal or monoclonal), drugs acting on immunophls (e.g., ciclosporin, Tacrolimus or Sirolimus). Additional drugs include interferons, opioids, TNF binding proteins, mycophenolate and small biological agents.

Examples of immunosuppressive drugs include: mesenchymal stem cells, anti-lymphocyte globulin (ALG) polyclonal antibody, anti-thymocyte globulin (ATG) polyclonal antibody, azathioprine, BAS1 L1X1MAB® (anti-I L-2Ra receptor antibody), cyclosporin (cyclosporin A), DACLIZUMAB® (anti-I L-2Ra receptor antibody), everolimus, mycophenolic acid, RITUX1MAB® (anti-CD20 antibody), sirolimus, tacrolimus, Tacrolimus and or Mycophenolate mofetil.

Antibiotics may be administered to the subject prior to, concurrently with and/or following treatment. Examples of antibiotics include Oflox, Gentamicin, Chloramphenicol, Tobrex, Vigamox or any other topical antibiotic preparation authorized for ocular use.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al., (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al., (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990);

Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Figure 1B:
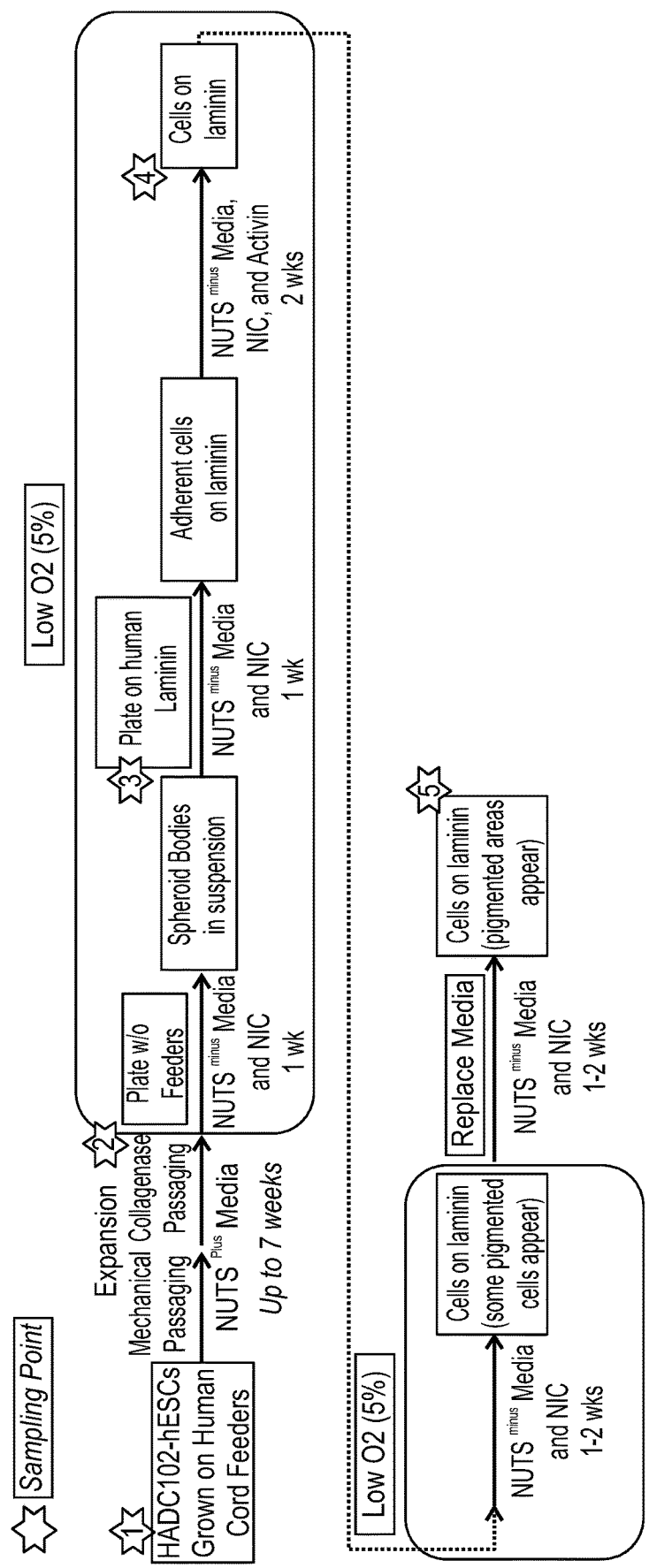
Figure 2B:
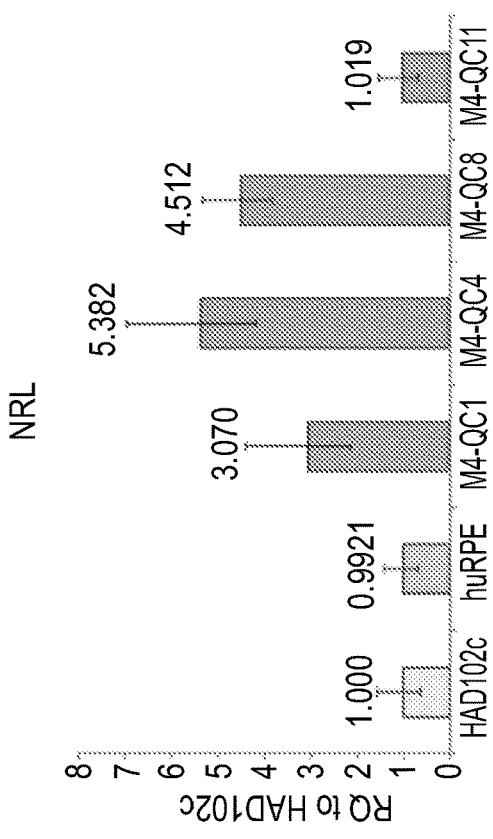
FIGS. 2A-F are graphs illustrating the upregulated expression of Chx10 (FIG. 2A), Nrl (FIG. 2B) Rhodopsin (FIG. 2C), Rax (FIG. 2D), MITF (FIG. 2E) and Recoverin (FIG. 2F) following differentiation of hESCs with Nicotinamide and Activin A.
Figure 2D:
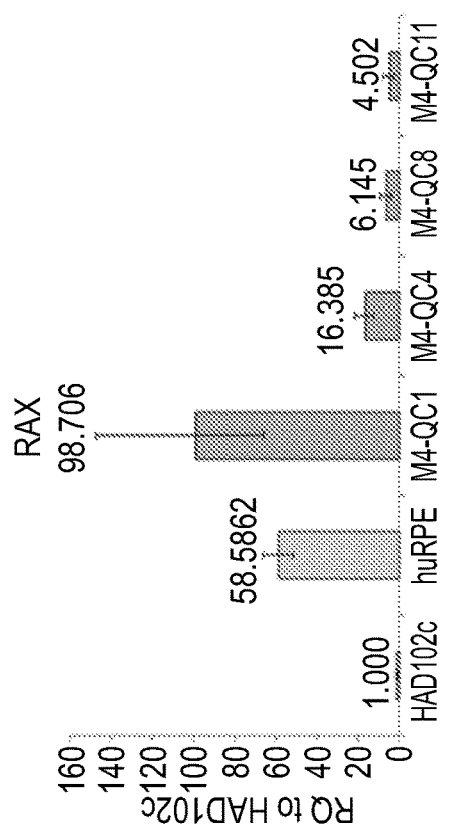
Figure 2A:
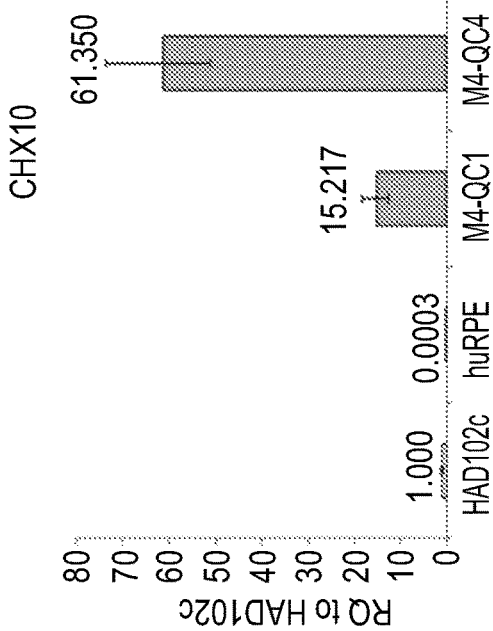
Figure 2C:
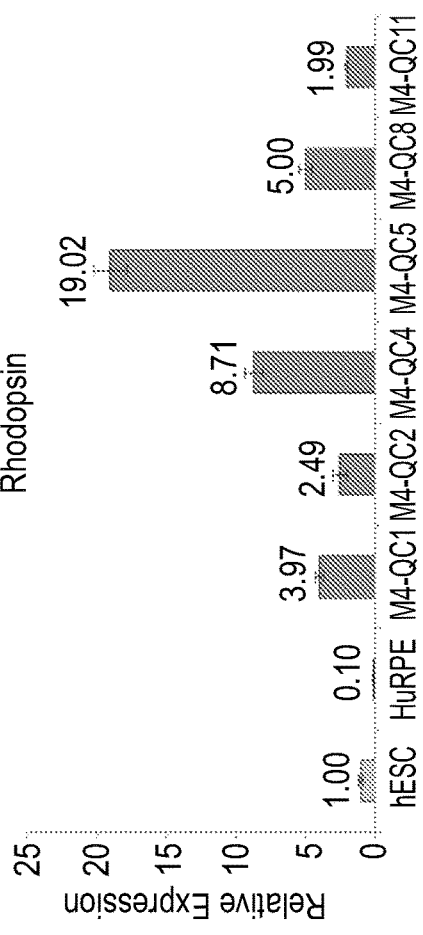
Figure 2F:
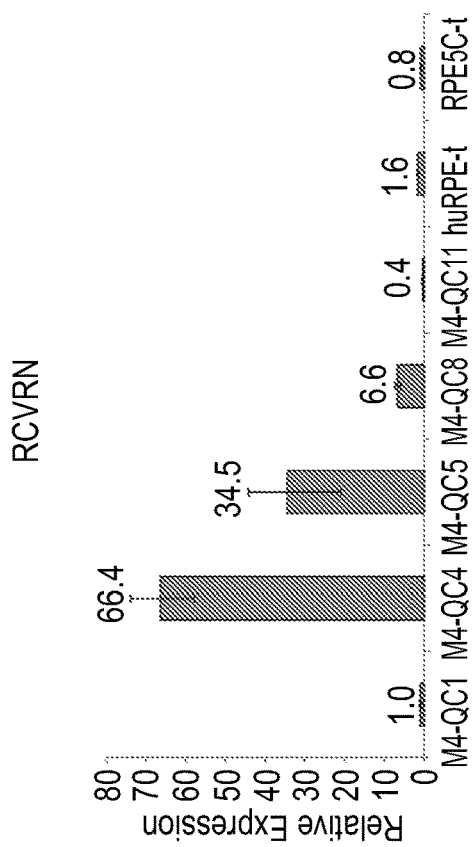
Figure 2E:
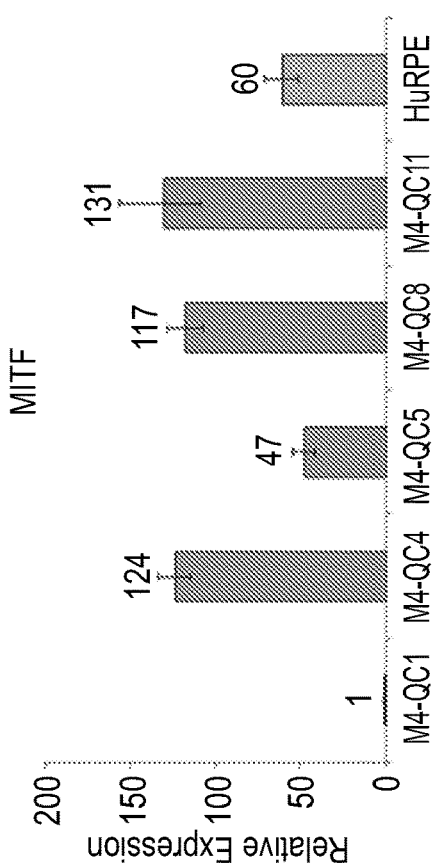
Figure 3D:
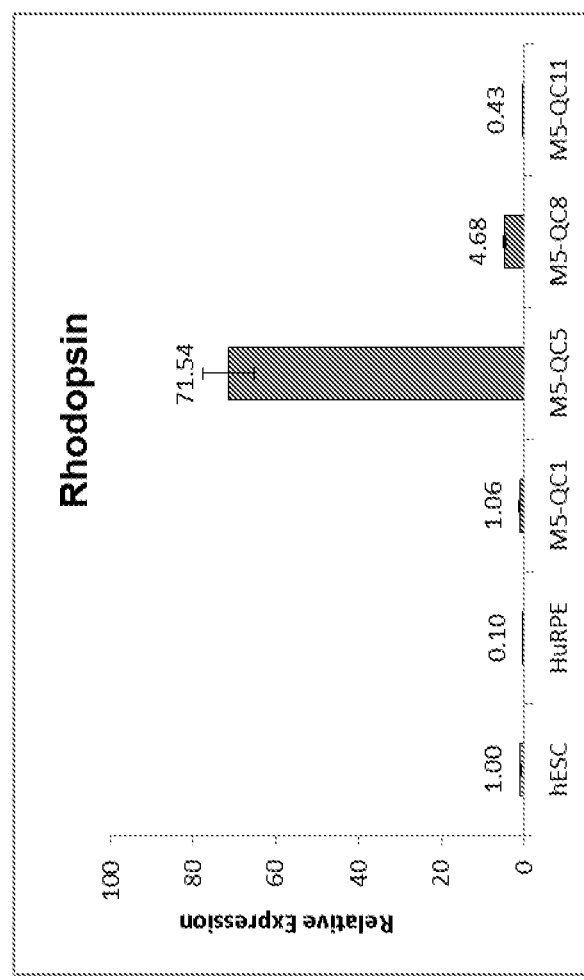

Generation of photoreceptors: Xeno-free GMP grade HAD-C 102 hESCs were expanded as colonies on irradiated xeno-free GMP-grade human umbilical cord fibroblast feeders (Stage I). Expanded hESCs were then transferred to a suspension culture to initiate differentiation in a directed manner in the presence of nicotinamide (Stage II). Spheroid bodies (SBs) were formed and then plated as an adherent cell culture under continued directed differentiation conditions (initially in the presence of nicotinamide alone, and subsequently in the presence of nicotinamide and activin A) towards a neural fate and subsequently towards a photoreceptor cell fate (Stage II)—see FIG. 1B.

Generation of RPE Cells: See FIG. 1A.

Quantitative Real Time PCR (QRT-PCR): QRT-PCR assays were carried out with TaqMan Fast Universal PCR Master Mix (Cat. #AB-4366072) using gene specific TaqMan assays (see Table 1). PCR reaction was done in Optical 96-well Fast Thermal Cycling plates (Cat. #AB-4314320) using the Applied Biosystems 7900HT Fast Real-Time PCR instrument. Analyses of Real Time PCR results were based on Applied Biosystems (ABI) protocol. 50 ng of cDNA templates were used in triplicates for each assay. Acquisition was carried out by Real Time automated machine 7900HT using the Sequence Detection System version 2.3 (or version 2.4 ABI). The resulted Ct values are the cycle numbers at which the PCR signal for each sample is detected above the threshold.

Within each test condition, the expression of each marker was normalized to the house keeping gene (Human GUSB; β-glucuronidase, Hs00939627_m1) endogenous control. ΔCt is the cycle number following the normalization. To compare the relative quantity of each marker at the various conditions tested, the RQ Manager Software version 1.2 (or version 1.2.1 ABI) was used, with the ΔΔCt algorithm (according to Livak and Schmittgen, 2001). The averaged relative expression was calculated automatically according to the formula: 2-ΔΔCt, where ΔΔCt is the cycle number after normalization to the endogenous control and to a reference control (set as 1 in each bar graph). Computer results pellets ("Amplification data" export files) were transferred to Excel for further analyses. Test repeats were averaged and displayed with Min and Max error bars.

Rhodopsin QRT-PCR assay was carried out using the hard-shell thin-wall 96 well PCR plates (Bio-Rad, Cat. #HSP 9601) and the Bio-Rad Fast Real-Time PCR instrument. Acquisition and analysis were carried out by Real Time automated machine Bio-Rad CFX96 using the CFX Manager Software version 3.1. Analyses of Real Time PCR results were based on Bio-Rad protocol. Computer results pellets ("Gene Expression Results" export files) were transferred to Excel for further analyses. Test repeats were averaged and displayed with Min and Max error bars.

TABLE 1

QRT-PCR Assay IDs

| Probe/Gene | QRT-PCR Assay ID |
| --- | --- |
| RAX | Hs00429459_m1 |
| CHX10 | Hs01584047_m1 |
| Rhodopsin | Hs00172997_m1 |
| NRL | Hs00172997_m1 |
| MITF | Hs0111294_m1 |
| RCVRN (Recoverin) | Hs00610056_m1 |

Figure 4:
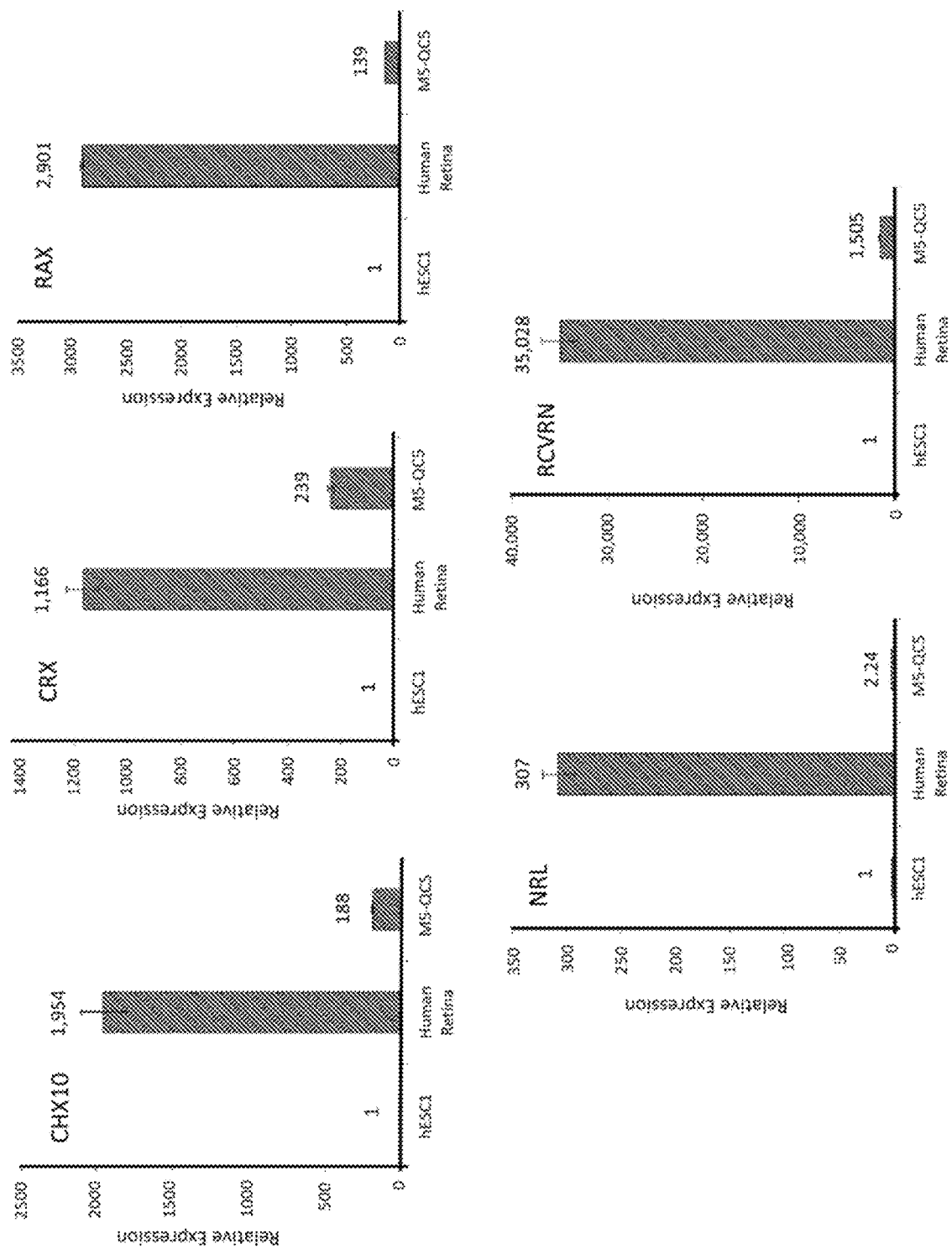
FIG. 4 are graphs illustrating the specificity of the probes that were used in assessment of retinal markers.

The specificity of the markers which were analyzed for retinal cells is illustrated in FIG. 4.

Results

The relative expression of the eye field marker Rax, the neural retina/photoreceptor progenitor markers Chx10 and Nrl, and the photoreceptor markers Rhodopsin and Recoverin at the various IPC points along the RPE production process were tested by QRT-PCR. As can be seen in FIGS. 2A-F, cells after nicotinamide and activin A treatment (IPC point 4/5) highly expressed Chx10 and upregulate Nrl, Recoverin and Rhodopsin relative to hESCs and human RPE and as well as relative to cells at later stages of the differentiation process following selection of pigmented cells and expansion (IPC point 8, cells at P0 and IPC point 11, cells at P2 post cryopreservation). Rax was expressed to some extent in the partially differentiated hESCs and following activin A (relative to RPE). The RPE marker MITF increased as the pigmented cells were expanded.

Similar data were received in a second experiment at the end of the differentiation phase (FIGS. 3A-D). As shown in FIGS. 3A-D, while chx10, rhodopsin and Nrl expression was downregulated following the isolation and expansion of pigmented cells, MITF was upregulated.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a retinal disease in a subject in need thereof comprising: (a) culturing a population of human pluripotent stem cells in a medium comprising a differentiating agent to obtain differentiating cells; (b) culturing said differentiating cells in a culture system comprising a medium which comprises one or more members of the transforming growth factor beta (TGFβ) superfamily, thereby generating a mixed population of cells comprising retinal pigment epithelial (RPE) cells and photoreceptors; (c) enriching for said photoreceptors in said mixed population of cells so as to generate a photoreceptor-enriched population of cells comprising at least about 75% photoreceptors; and (d) administering a therapeutically effective amount of said photoreceptor-enriched population of cells to the subject, thereby treating the retinal disease;

wherein step (a) comprises:
i) culturing the cultured population of human pluripotent stem cells in a medium comprising nicotinamide, in the absence of activin A under non-adherent conditions to generate a cluster of cells comprising differentiating cells; and subsequently;
ii) culturing the differentiating cells of (i) in a medium comprising nicotinamide, in the absence of activin A under adherent conditions.

2. A method of treating a retinal disease in a subject in need thereof comprising: (a) culturing a population of human pluripotent stem cells in a medium comprising a differentiating agent to obtain differentiating cells; (b) culturing said differentiating cells in a culture system comprising a medium which comprises one or more members of the transforming growth factor beta (TGFβ) superfamily, thereby generating a mixed population of cells comprising retinal pigment epithelial (RPE) cells and photoreceptors, wherein at least 10% of said mixed population of cells are photoreceptors; (c) isolating the photoreceptors from the mixed population of cells using surface markers for photoreceptors and (d) administering a therapeutically effective amount of the isolated photoreceptors to the subject, thereby treating the retinal disease;

wherein step (a) comprises:
i) culturing the cultured population of human pluripotent stem cells in a medium comprising nicotinamide, in the absence of activin A under non-adherent conditions to generate a cluster of cells comprising differentiating cells; and subsequently;
ii) culturing the differentiating cells of (i) in a medium comprising nicotinamide in the absence of activin A under adherent conditions.

3. The method of claim 2, further comprising cryopreserving said mixed population of cells following step (b) and prior to step (c).

4. The method of claim 3, wherein said cryopreserving is effected in a cryopreservative medium comprising dimethyl sulfoxide (DMSO).

5. The method of claim 4, wherein said cryopreservative medium is 90% Human Serum/10% dimethyl sulfoxide (DMSO).

6. The method of claim 2, wherein said medium of step (b) comprises nicotinamide and activin A.

7. The method of claim 6, further comprising a step of culturing said photoreceptors in a medium comprising nicotinamide and devoid of activin A following step (b) and prior to step (c).

8. The method of claim 2, wherein said transplanting is effected at the subretinal space of the eye.

9. The method of claim 2, wherein said cells are transplanted in a suspension, or as a monolayer of cells immobilized on a matrix or a substrate.

10. A method of generating photoreceptors comprising: (a) culturing a population of human pluripotent stem cells in a medium comprising a differentiating agent to obtain differentiating cells; (b) culturing said differentiating cells in a culture system comprising a medium which comprises one or more members of the TGFβ superfamily, thereby generating a mixed population of cells comprising retinal pigment epithelial (RPE) cells and photoreceptors; (c) enriching for said photoreceptors in said mixed population of cells so as to generate a photoreceptor-enriched population of cells comprising at least about 75% photoreceptors; and (d) expanding said photoreceptor-enriched population of cells, wherein step (a) comprises:
i) culturing the cultured population of human pluripotent stem cells in a medium comprising nicotinamide, in the absence of activin A under non-adherent conditions to generate a cluster of cells comprising differentiating cells, and subsequently,
ii) culturing the differentiating cells of (i) in a medium comprising nicotinamide, in the absence of activin A under adherent conditions.

11. The method of claim 10, further comprising expanding said human pluripotent stem cells prior to step (a), and expanding said population of photoreceptors following step (c) and prior to step (d).

12. The method of claim 11, wherein said human pluripotent stem cells are expanded on feeder cells and wherein said feeder cells comprise human cord fibroblasts.

13. The method of claim 10, wherein said human pluripotent stem cells comprise human embryonic stem cells (ESCs) or induced pluripotent stem cells (iPSCs).

14. The method of claim 10, wherein said member of the TGFβ superfamily is selected from the group consisting of TGFβ1, TGFβ3 and activin A.

15. The method of claim 10, wherein said non-adherent conditions comprise a non-adherent culture plate or a non-adherent substrate.

16. The method of claim 10, wherein step (a) further comprises dissociating said cluster of cells prior to step (ii) to generate clumps of cells or a single cell suspension of cells.

17. The method of claim 10, wherein step (a) is effected for at least one day and wherein step (b) is effected for at least one day.

18. The method of claim 10, wherein at least a portion of said culturing is effected under conditions wherein the atmospheric oxygen level is less than about 10% and wherein said culturing is effected under conditions wherein the atmospheric oxygen level is greater than about 10%.

19. The method of claim 10, wherein the differentiating cells comprise cells that are co-differentiating.

* * * * *